US011535877B2

(12) United States Patent
Thompson et al.

(10) Patent No.: US 11,535,877 B2
(45) Date of Patent: Dec. 27, 2022

(54) METHOD FOR THE HYDROLYSIS OF LIGNOCELLULOSIC BIOMASS (71) Applicant: FIBERIGHT LIMITED, Gwent (GB)

(72) Inventors: Nicholas Mark Thompson, Longtown (GB); Dhivya Jyoti Puri, Hampshire (GB); Peter Speller, Llanishen (GB)

(73) Assignee: FIBERIGHT LIMITED, Gwent (GB)

( * ) Notice: Subject to any disclaimer, the term of this patent is extended or adjusted under 35 U.S.C. 154(b) by 100 days.

(21) Appl. No.: 16/608,253

(22) PCT Filed: Apr. 27, 2018

(86) PCT No.: PCT/EP2018/025132
§ 371 (c)(1),
(2) Date: Oct. 25, 2019

(87) PCT Pub. No.: WO2018/197051
PCT Pub. Date: Nov. 1, 2018

(65) Prior Publication Data
US 2020/0181662 A1 Jun. 11, 2020

(30) Foreign Application Priority Data
Apr. 28, 2017 (GB) .................................... 1706831

(51) Int. Cl.
*C12P 19/14* (2006.01)
*C12N 9/42* (2006.01)
*C12P 7/16* (2006.01)
*C12P 7/46* (2006.01)
*C12P 7/56* (2006.01)
*C12P 19/02* (2006.01)
*C12P 7/10* (2006.01)

(52) U.S. Cl.
CPC ............ *C12P 19/14* (2013.01); *C12N 9/2437* (2013.01); *C12P 7/10* (2013.01); *C12P 7/16* (2013.01); *C12P 7/46* (2013.01); *C12P 7/56* (2013.01); *C12P 19/02* (2013.01); *C12P 2201/00* (2013.01); *C12P 2203/00* (2013.01)

(58) Field of Classification Search
None
See application file for complete search history.

(56) References Cited

U.S. PATENT DOCUMENTS

| | | | | |
|---|---|---|---|---|
| 5,100,066 A | * | 3/1992 | Frei ..................... | B03B 9/061 241/21 |
| 2010/0255554 A1 | | 10/2010 | Benson et al. | |
| 2014/0227757 A1 | * | 8/2014 | Jin ...................... | C12P 7/10 435/165 |
| 2014/0242657 A1 | | 8/2014 | Ropars et al. | |
| 2016/0244788 A1 | * | 8/2016 | Retsina ................. | C13K 1/02 |
| 2016/0333333 A1 | * | 11/2016 | Showmaker ......... | C12N 9/2434 |
| 2016/0376621 A1 | | 12/2016 | Benson et al. | |

FOREIGN PATENT DOCUMENTS

| | | |
|---|---|---|
| EP | 0 423 606 | 4/1991 |
| WO | 2009/095781 | 8/2009 |
| WO | 2010/111775 | 10/2010 |
| WO | 2010/135365 | 11/2010 |
| WO | 2011/080154 | 7/2011 |
| WO | 2016/062646 | 4/2016 |
| WO | 2016/134195 | 8/2016 |
| WO | 2017/098247 | 6/2017 |

OTHER PUBLICATIONS

Chen et al., Enzymatic hydrolysis of corncob and ethanol production from cellulosic hydrolysate, Int. Bioderioration Biodegradation 59, 2007, 85-89. (Year: 2007).*
Bharathiraja et al., Insights on Lignocellulosic Pretreatments for Biofuel Production—SEM and Reduction of Lignin Analysis, Int. J. ChemTech. Res. 6, 2014, 4334-44. (Year: 2014).*
Montella et al., Saccharification of newspaper waste after ammonia fiber expansion or extractive ammonia, AMB Expr. 6, 2016, 18. (Year: 2016).*
Taherzadeh et al., Pretreatment of Lignocellulosic Wastes to Improve Ethanol and Biogas Production, Int. J. Mol. Sci. 9, 2008, 1621-51. (Year: 2008).*
Van Dyk et al., A review of lignocellulose bioconversion using enzymatic hydrolysis and synergistic cooperation between enzymes, Biotechnol. Adv. 30, 2012, 1458-1480. (Year: 2012).*
Kumar et al., Effects of Cellulase and Xylanase Enzymes on the Deconstruction of Solids from Pretreatment of Poplar by Leading Technologies, Biotechnol. Prog. 25, 2009, 302-14. (Year: 2009).*
Wayman et al., Bioconversion of waste paper to ethanol, Process Biochem. 27, 1992, 239-45. (Year: 1992).*
Puri et al., Process improvement for the production of fermentable sugars using paper pulp derived from municipal solid waste, Ph.D. thesis, University of Southampton, 2014. (Year: 2014).*
International Search Report and Written Opinion of the International Searching Authority, dated Nov. 7, 2018 in corresponding International Application No. PCT/EP2018/025132.
Olofsson et al., "Improving simultaneous saccharification and co-fermentation of pretreated wheat straw using both enzyme and substrate feeding", Biotechnology for Biofuels, 3(17): 1-9 (2010).
Puri et al., "Improving the performance of enzymes in hydrolysis of high solids paper pulp derived from MSW", Biotechnology for Biofuels, 6(107): 1-10 (2013).

(Continued)

*Primary Examiner* — Robert B Mondesi
*Assistant Examiner* — Todd M Epstein
(74) *Attorney, Agent, or Firm* — Wenderoth, Lind & Ponack, L.L.P.

(57) ABSTRACT

The present invention relates generally to the field of industrial biotechnology and particularly to an improved hydrolysis method for increasing sugar production from a high solids concentration of lignocellulosic biomass, especially one derived from Municipal Solid Waste (MSW) by enzymatic hydrolysis of a lignocellulosic biomass to obtain a slurry, wherein the hydrolysis comprises aliquot additions of enzyme and lignocellulosic biomass; and removal of sugars from the slurry and washing of the residual lignocellulosic biomass.

22 Claims, 4 Drawing Sheets

(56) References Cited

OTHER PUBLICATIONS

Office Action and Search Report, dated Jan. 30, 2019 in corresponding UK patent application No. GB1806922.9.
Jung et al., "Fed-Batch Enzymatic Saccharification of High Solids Pretreated Lignocellulose for Obtaining High Titers and High Yields of Glucose", Appl Biochem Biotechnol, 182: 1108-1120 (2017).
Jensen et al., "Cellulase Hydrolysis of Unsorted MSW", Appl Biochem Biotechnol, 165: 1799-1811 (2011).
Kemppainen et al., "Hydrolysis and composition of recovered fibres fractionated from solid recovered fuel", Biosource Technology, 169: 88-95 (2014).
Kitcherside et al., "FibreCap: an improved method for the rapid analysis of fibre in feeding stuffs", Animal Feed Science and Technology, 86: 125-132 (2000).
Sluiter et al., "Determination of Structural Carbohydrates and Lignin in Biomass", National Renewable Energy Laboratory, Golden, Colorado, Technical Report NREL/TP-510-42618, Laboratory Analytical Procedure (LAP): 1-15 (2008; Revised Aug. 2012).
Wang et al., "Effect of calcium carbohydrate in waste office paper on enzymatic hydrolysis efficiency and enhancement procedures", Korean J. Chem. Eng. 28(2): 550-556 (2011).
Xue et al., "Strategies to recycle enzymes and their impact on enzymatic hydrolysis for bioethanol production", Bioresources, 7(1): 602-615 (2012).

\* cited by examiner

METHOD FOR THE HYDROLYSIS OF LIGNOCELLULOSIC BIOMASS

TECHNICAL FIELD

The present invention relates generally to the field of industrial biotechnology and particularly to an improved hydrolysis method for increasing sugar production from a lignocellulosic biomass, especially one derived from Municipal Solid Waste (MSW).

BACKGROUND

Commercial, industrial and residential consumers generate large amounts of waste, and although national and local governments in many parts of the world impose strict recycling requirements on households, a large part of this waste still ends up in landfill or is incinerated, which results in missed opportunities to obtain valuable products from the waste matter.

There is the potential for many such valuable products to be obtained from the lignocellulosic matter found in MSW. Lignocellulosic material has a significant sugar potential in the form of cellulose and hemicellulose and this can be accessed using enzymatic hydrolysis. For example, lignocellulosic materials can be converted to fermentable sugars and subsequently to biofuels, such as bioethanol. The demand for bioethanol is met today using bioethanol crops such as sugar cane and corn, but it would be highly advantageous to be able to generate bioethanol from MSW as a starting material rather than taking up valuable land for growing dedicated bioethanol crops, which land could otherwise be used to grow food. Meeting the demand for biofuels using MSW could play an important role in terms of increasing food security and also in terms of reducing the amount of material sent to landfill.

Other valuable products, such as specialty chemicals (e.g. bio-resins, lactic acid, butanol, succinic acid etc.) could also be derived from the lignocellulosic materials found in MSW.

The conversion of lignocellulosic materials to fermentable sugars is possible, but barriers remain when it comes to implementing the process on a commercial scale and making the process economically viable. In order to make the process economically viable, it would be important to maximise sugar yields while at the same time making efficient use of resources, such as energy, water and enzymes. Furthermore, additional challenges may present themselves when the lignocellulosic material comes from MSW. Such challenges may arise from contaminants from the mixed waste stream and variability of the feedstock.

The present invention aims to solve the aforementioned problems by providing an improved hydrolysis method for increasing sugar production from a lignocellulosic biomass, especially lignocellulosic biomass derived from MSW. The invention further aims to provide a method that is economically viable, particularly on a commercial scale.

SUMMARY

According to the present invention, there is provided a method for increasing sugar yield from a high solids concentration of lignocellulosic biomass and/or for reducing enzyme quantity, the method comprising:
 a. enzymatic hydrolysis of a lignocellulosic biomass to obtain a slurry, wherein the hydrolysis comprises aliquot additions of enzyme and lignocellulosic biomass; and
 b. removal of sugars from the slurry and washing of the residual lignocellulosic biomass.

The invention also provides sugar(s) obtainable by the method of the invention.

The invention also provides lignin-rich solids (refered to herein as "residual lignocellulosic biomass" or post hydrolysis solids (PHS), which terms are used interchangably herein) obtainable by the method of the invention, which PHS have a higher calorific value relative to PHS obtained from conventional methods for the hydrolysis of a lignocellulosic biomass and/or relative to the original lignocellulosic biomass starting material.

Also provided is the use of such sugars for biogas production and/or PHS for gasification or pyrolysis. The sugars and/or PHS may be used to create value added products, such as specialty chemicals, e.g. bio-resins, lactic acid, butanol, succinic acid etc.

Also provided is a method for making fuel, comprising converting a high solids concentration of lignocellulosic biomass, preferably obtained from MSW, by performing the method of the invention to obtain sugars and/or PHS; and the use of sugars in biogas production and the use of PHS in gasification or pyrolysis.

The invention also provides use of a surfactant, such as PEG, for reducing the enzyme quantity needed during hydrolysis of a lignocellulosic biomass (particularly from MSW) and/or for increasing sugar yield from a lignocellulosic biomass (particularly from MSW).

The invention also provides a hitherto unknown composition for use in enzyme hydrolysis of a lignocellulosic biomass, particularly from MSW, comprising cellulases and at least one surfactant and/or phosphoric acid and/or biocide agents such as chlorine dioxide, Benzoisothiazolinone, virginiamiacin and/or buffering agents such as calcium carbonate.

Also provided is a biorefinery for refining a high solids concentration of lignocellulosic biomass, preferably obtained from MSW, by performing the method of the invention to produce sugars, fuel, feed for biogas production, gasification or pyrolysis, and for example, to create value added products, such as specialty chemicals e.g. bio-resins, lactic acid, butanol, succinic acid etc.

DETAILED DESCRIPTION

According to a first aspect of the present invention, there is provided a method for increasing sugar yield from a high solids concentration of lignocellulosic biomass and/or for reducing enzyme quantity, the method comprising:
 a. enzymatic hydrolysis of a lignocellulosic biomass to obtain a slurry, wherein the hydrolysis comprises aliquot additions of enzyme and lignocellulosic biomass; and
 b. removal of sugars from the slurry and washing of the residual lignocellulosic biomass.

According to a preferred embodiment, the lignocellulosic biomass is obtained from MSW comprising a lignocellulosic component. MSW is the typical waste generated by households and commercial establishments, such as offices, schools, warehouses, restaurants, retail establishments and any non-hazardous industrial waste, including residues from other waste recycling activities. Typical MSW includes any of the following: paper, cardboard, plastics, metals, glass, batteries, appliances, textiles, rubber, wood, garden and food waste. The terms "mixed waste", "general waste", "household waste", "waste", "Municipal Solid Waste" and "MSW" are all used interchangeably herein to mean any two, three, four, five, six, seven, eight, nine, ten or more of the following: paper, cardboard, plastics, metals, batteries, appliances, glass, textiles, rubber, wood, garden and food waste and comprising lignocellulosic material. The term "lignocellulosic" biomass/material/matter/component or "lignocellulose", as defined herein, refers to biomass principally comprising cellulose, hemicelluloses, and lignin, but also comprising polysaccharides, phenolic polymers and proteins. Lignocellulose from MSW mainly comes from discarded paper, cardboard and plant matter. Lignocellulose derived from MSW also contains a small percentage of pseudo-lignin. The pseudo lignin content is a fraction of the "lignin" as determined by the standard NREL method for lignocellulose composition: Determination of structural carbohydrates and lignin in Biomass, Sluiter et al. (2012) http://www.nrel.gov/docs/gen/fy13/42618.pdf. The make-up of pseudo-lignin includes, but is not limited to plastics, clays, complexed lignin, virgin lignin and paper making additives.

Prior to the first enzymatic hydrolysis step, any non-reactive products such as plastics, glass and metal contaminants are removed from the MSW, thereby increasing the lignocellulosic content of the material. Any method may be used to obtain the lignocellulose component from MSW and a preferred method is as outlined below and as further described in International patent application No. WO 2017/098247, the contents of which are incorporated herein by reference as if fully set forth.

The lignocellulose component from MSW may be obtained by:
  (a) separating MSW into at least two parts, comprising: (i) mainly food waste (fines) and (ii) mainly paper and other recyclable material (overs);
  (b) pulping the overs; and
  (c) washing the overs to obtain a cellulose-rich biomass; and optionally
  (d) processing the fines to obtain a cellulose-rich biomass.

Following removal of the non-reactive products, the remaining waste matter may undergo one or more optional pre-treatments prior to enzymatic hydrolysis. Such a pre-treatment may, for example, help facilitate the breakdown and/or subtantial removal of lignin, which is known to be particularly recalcitrant, and/or pseudo lignin, and help improve accessibility to the cellulose ready for enzyme hydrolysis. Any available pre-treatment may be used, for example, a physical treatment, such as milling, irradiation or ultrasound and/or a physico-chemical treatment, such as explosion (either with or without catalysts such as sulphur dioxide or ammonia), alkali, acid, gas, liquid hot water (LHW) cooking, oxidising agents and solvent extraction treatments.

Certain pre-treatments were tested by the inventors but were surprisingly found not to enhance conversion. For example, reducing particle size by milling (to 0.5>0.1 mm) did not enhance conversion, and in fact hindered the process. Mild alkali treatment also led to a significant decrease in conversion. The method according to the present invention therefore does not comprise pre-treatment by milling or any mild alkali treatment. Any reference herein to "conversion" is taken to mean the conversion of the substrate (here a lignocellulosic biomass, preferably obtained from MSW) to sugars and/or PHS.

Solvent extraction on the other hand was found to increase conversion. Solvent extraction was carried out to substantially remove extractives such as waxes and oils and/or pseudo lignin. Solvent extraction with acetone was found to be particularly favourable and resulted in an increase of up to 6% in conversion compared to unextracted pulp. Ionic liquids may also be used in place of acetone to obtain a substantially extractive and/or lignin-free cellulose pulp. According to the present invention, there is provided a method as defined herein comprising a solvent extraction pre-treatment prior to enzymatic hydrolysis, particularly with acetone, to substantially remove extractives or pseudo lignin. Solvent extraction may even have a dual benefit of helping to remove extractives and/or pseudo lignin as well as recovering value-added compounds or building blocks for other industrial processes, such as the pharmaceutical industry.

The lignocellulosic material, either with or without any pre-treatment, is then subjected to enzymatic hydrolysis for the production of monomeric and oligomeric sugars. Methods for enzymatic hydrolysis are known and any such known method may be used in the hydrolysis steps of the method of the invention.

In general, enzymatic hydrolysis of a lignocellulosic material typically involves cooking and/or pre-treating the substrate to enhance its biodegradability, followed by incubating the cooked and/or pre-treated substrate with the addition of suitable enzymes for a number of days and centrifugation or filter pressing of the incubated mixture to separate out the sugars therefrom.

Figure 1:
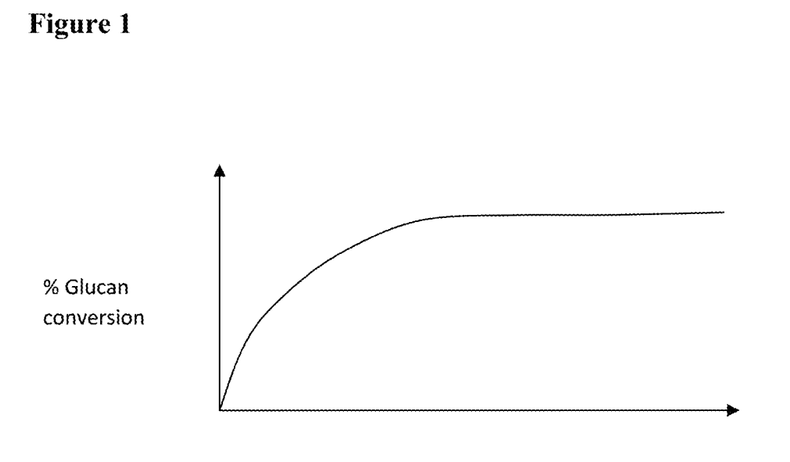
FIG. 1 shows a typical hydrolysis curve where the initial rate of reaction is fast and conversion then plateaus to a maximum level.

The hydrolysis behaviour of the MSW pulp was found by the inventors to be similar to that of other lignocellulosic substrates. For example, the hydrolysis rate was initially rapid but then decreased with time due to "the solids effect" where increased solids content led to an overall decrease in percentage sugar conversion. An increase in enzyme dosing did not lead to a proportional increase in substrate conversion. FIG. 1 shows a typical hydrolysis curve, where the rate of hydrolysis decreases with time and the process usually ends before complete hydrolysis of the substrate. This plateau in hydrolysis normally occurs within 12-72 hours depending on the substrate concentration used. Although it is possible to get 100% conversion at low solid concentrations (less than 5% TS), the percentage conversion decreases as the solids content increases.

Cellulose and hemicellulose components of the lignocellulosic material can be broken down into monomeric and oligomeric sugars by cellulase and hemicellulase enzymes. The enzymes used in the hydrolysis reaction may advantageously be any cellulases and/or hemicellulases (eg; xylanases and mannases). Preferably, both cellulases and hemicellulases are used.

In a cellulase enzyme mixture which breaks cellulose down into monomeric glucose there are 4 main classes of enzyme:
  1) Endoglucanases—These enzymes cut up insoluble cellulose fibres into smaller chains;
  2) Cellobiohydrolases—These enzymes move along the cut insoluble chains to produce soluble cellobiose and cellotriose;
  3) β-glucosidase—this enzyme breaks the cellobiose and triose into glucose monomers;
  4) lytic polysaccharide monooxygenases ((LPMOS) e.g. AA9) This complex helps to increase enzyme activity by using a redox mechanism.

The two most commonly used commercial preparations of cellulases and hemicellulases are those from Novozymes (Cellic C-Tec family) and Genencore (Accelerase).

The quantity of cellulase enzymes used for the hydrolysis reaction range from between about 5-50 mg enzyme g-1 pulp. Hydrolysis is preferably carried out in the range of from between about 40° C. to about 60° C., preferably about 50° C. to about 55° C. The reaction mixture is preferably maintained between about pH 4 to about pH 6, preferably about pH 5. Hydrolysis may last for up to 4 days and is preferably completed within 2 days (about 48 hours).

According to a preferred embodiment, enzymatic hydrolysis of the lignocellulosic biomass takes place in the presence of one or more surfactants and/or nitrogen additives, such as polyethylene glycol (PEG), Tween, glycine etc. The use of surfactants and/or nitrogen additives was surprisingly found by the inventors to allow for a decrease in the amount of enzyme required and/or an increase in sugar yield and/or improved dewaterability. These findings were surprising given conflicting literature on the effect of using surfactants: for example Xue et al., 2012 found that surfactants increase conversion and enzyme recycling efficiency on soft wood substrates but not on hardwoods (Xue et al., 2012a). Furthermore, some previous studies showed that the use of PEG did not enhance conversion (see Jensen et al., 2011; Kemppainen et al., 2014).

According to the present invention, enzymatic hydrolysis in the presence of one or more surfactants and/or nitrogen additives, particularly PEG, allows for a decrease in enzyme requirement, meaning that the same or increased sugar yields may be obtained with less enzyme, for example, about 10% less, 20% less, 30% less, 40% less, 50% less enzyme compared to control reactions.

Additionally or alternatively, enzymatic hydrolysis in the presence of one or more surfactants and/or nitrogen additives, particularly PEG, gives an increase in sugar yields of anything up to about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or up to about 100% or more compared to control reactions.

Additionally or alternatively, enzymatic hydrolysis in the presence of one or more surfactants and/or nitrogen additives, particularly PEG, improves dewaterability by at least 10%, 11%, 12%, 13%, 14%, 15%, 16%, 17%, 18%, 19%, 20%, 21%, 22%, 23%, 24%, 25%, 26%, 27%, 28%, 29%, 30% or more relative to control reactions.

According to a preferred embodiment, the surfatctant used during enzymatic hydrolysis is PEG. The PEG is preferably PEG 6000, but PEG with other molecular weights may be equally suitable.

Preferably, the surfactant (e.g. PEG (6000)) and/or nitrogen additive is used in the hydrolysis reaction in an amount ranging from between about 0.1-2% per g dry substate (MSW).

The inventors found that PEG 6000 increased conversion at a high solids concentration (20% Total Solids (TS)) by 15% over 48 hours while allowing a 40% decrease in the enzyme requirement. According to the inventor's calculations, a 40% decrease in enzyme loading afforded by PEG could allow a cost saving of approximately US $55 per tonne of pulp. In the context of a full-scale plant processing 200 tonnes per day this could lead to an annual cost saving of US $4 million. Improvements would similarly occur at lower solid concentrations.

Other factors were also tested for their effect on hydrolysis. For example, pH control with or without buffer was looked at and it was surprisingly found that an increase in glucan conversion was obtained by using phosphoric acid for pH control compared to using citric acid buffer. The cooking of lignocellulosic pulp derived from MSW in water adjusted to pH 5 with phosphoric acid increased conversion. When pH 5 cooking was carried out at a temperature in the range of between about 80 and 120° C., conversion was found to increase by at least 5% compared to cooking the lignocellulose in a citric acid buffer solution.

In addition to the benefits discussed above, agitation was found to be important in achieving higher hydrolysis yields. Not all agitation methods however gave equal results and agitation by tumbling or gravity mixing was found to give better results than orbital shaking and rotational mixing. Agitation in a continuous stirred tank reactor (CSTR) was found to be optimal when using hydrofoil or pitched blade impellers. According to a further embodiment, enzymatic hydrolysis may be conducted with at least some degree of agitation, particularly agitation by tumbling or gravity mixing.

Substrate feeding strategies were also investigated and it was found that at high solids concentrations, aliquot additions of enzyme and lignocellulosic biomass were superior (i.e. allowed for increased conversion and/or a reduction in enzyme quantities) compared to batch hydrolysis or all enzyme upfront methods and compared to aliquot addition of solids alone.

According to a preferred embodiment, aliquots of wet substrate are fed together with aliquots of enzyme. Preferably, substrate is added to the reactor at a concentration in the range of of between about 5-8% TS, thereafter aliquot additions of enzyme and substrate (lignocellulosic biomass) take place simultaneously but the advantageous effect may also be realised so long as the enzyme and substrate are added within an hour of each other.

Preferably, at least two, at least three, at least four, at least five, at least six, at least seven, at least eight, at least nine or at least ten or more aliquot additions of enzyme and substrate are added during one hydrolysis reaction. For example, if the total quantity of cellulase enzymes used in a hydrolysis reaction is 10 mg enzyme g-1 pulp, this amount is divided (preferably equally) into the desired number of aliquots and added throughout the hydrolysis reaction, this may optionally be at fairly equal time intervals.

In a preferred embodiment, the majority of solids (optionally with enzymes) are added upfront (for example, more than 60%, 65%, 70%, 75%, 80% 85%, 90% or more), followed by subsequent smaller aliquot additions over the course of the reaction. Any surfactant and/or nitrogen additive to be used is also preferably added at the start of hydrolysis before enzyme addition but may also be added together with the enzyme and/or substrate additions.

Advantageously, enzymatic hydrolysis with aliquot additions of enzyme and substrate gives increased conversion and/or a reduction in enzyme quantities.

For example, a decrease in enzyme requirement allows for the same or increased sugar yields to be obtained with less enzyme, for example, about 10% less, 20% less, 30% less, 40% less, 50% less enzyme compared to other feeding strategies.

Additionally or alternatively, enzymatic hydrolysis with aliquot additions of enzyme and substrate allows for an increase in sugar yields of at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or at least 100% or more compared to other feeding strategies.

Any reference herein to "high solids" is taken to mean a total solids (TS) concentration of greater than 15%. Any reference herein to "low solids" is taken to mean a total solids concentration of less than 5%.

Some of the difficulties arising from the operation of a high solids hydrolysis process, as is the case when using MSW as a substrate, is the prevalence of the "solids effect" which may be caused by: insufficient mixing; product inhibition as a result of increasing sugar concentration; decreased water availability; irreversible binding of adsorbed enzyme to the substrate, including non productive binding to lignin; inhibition of enzyme adsorption; and enzyme denaturation. To overcome some of these limitations, process strategies to alleviate product inhibition and to increase water availability in the hydrolysis system were employed.

According to the method of the present invention, following enzymatic hydrolysis, sugars are removed from the post-hydrolysis slurry. The sugars may be removed by fermentation or direct removal, e.g. by centrifugation or filter press. Sugars may also be removed by Simultaneous Saccharification Fermentation (SSF). Fermentation was also found to alleviate product inhibition which reactivates the enzyme system. Fermentation is preferably carried out in the range of between about 20° C. to 70° C. or 20° C. to 40° C., preferably at about 30° C.

According to the method of the present invention, following removal of sugars from the slurry, the residual solids are washed. According to a preferred embodiment, the residual solids are washed in water and the wash water is then removed and replaced with an equal or preferably lower volume of water (preferably at about pH 5). This wash procedure advantageously reactivates the enzyme system and gives increased conversion compared to methods without such a wash step.

Furthermore, the wash water contains dilute amounts of sugar and it was found that this wash water could be used as dilution water in any further hydrolysis steps so as to increase total amounts of glucose obtained. Increasing the final glucose concentration in the sugar solution advantageously allows the costs associated with downstream production of biofuels and biochemicals to be reduced.

In addition, it was found that enzyme recovery in the wash water could be increased if the residual solid was washed at about pH 9 (rather than about pH 5). Employing such a wash water recycle strategy therefore increases sugar yields and reactivates the enzyme, thereby requiring reduced enzyme quantities.

According to a preferred embodiment, the residual solids, once washed, are resuspended in the aforementioned wash water or in fresh pH~5 water and subjected to a second hydrolysis step. Advantageously, such a second hydrolysis step does not require any enzyme addition, although in some cases the the addition of 8-glucosidase may be used to compensate for its loss while washing. A pH of about 9 was found to be particularly favourable for enzyme recovery from the wash water. A pH of about 5 was found to be particularly favourable for increased yields of glucose from this second stage hydrolysis.

The wash water preferably comprises a surfactant and/or nitrogen additive, preferably PEG (6000). Reuse of the wash water in subsequent hydrolysis steps is particularly preferred, although it may also be used for biogas production.

According to a preferred embodiment of the present invention, there is provided a method for increasing sugar yield from a high solids concentration of lignocellulosic biomass and/or for reducing enzyme quantity, the method comprising:

a. enzymatic hydrolysis of a lignocellulosic biomass to obtain a slurry, wherein the hydrolysis comprises aliquot additions of enzyme and lignocellulosic biomass; and b. removal of sugars from the slurry to leave a residual lignocellulosic biomass and washing of the residual lignocellulosic biomass; and c. resuspension of the washed residual lignocellulosic biomass in about pH 5.0-9.0 water or in the wash water of b. and hydrolysis (preferably without enzyme addition) to obtain a slurry; and optionally d. repeating steps b and c as needed.

Performance of the methods of the invention generates sugars comprising, for example, any one or more of glucose, xylose, mannose, galactose, arabinose and soluble oligosaccharides containing chains of monomeric sugars. Preferably, the sugar solution obtained by the method of the invention comprises glucose:xylose at a ratio of about 5-8:1 or 6-7:1. In contrast, sugars obtained from forestry or agricultural waste would have glucose:xylose ratios of 2-4:1. Grasses, for example, have more hemicellulose than forestry residues and so would give higher proportions of xylose than forestry residues.

Performance of the methods of the invention also generates a washed residual lignocellulosic biomass, which is a lignin-rich solid, also refered to herein as post hydrolysis solids (PHS).

The PHS comprises less than about 6% ash or less than about 7% ash or less than about 8% ash or less than about 9% ash or less than about 10% ash.

Additionally or alternatively, the PHS also comprises a lignin and/or pseudo lignin component. Studies carried out on the lignin component of PHS obtainable by the methods of the invention indicate it to be a high-quality lignin, meaning that the lignin maintains a high degree of its native structure. Conventional waste processing and hydrolysis tends to use harsh pre-treatments, such as autoclaving, which would alter the structure of the lignin. For the lignin to retain its native structure, the waste processing and/or hydrolysis methods preferably do not include any harsh treatments which require high temperatures (above 130° C.), high pressures (above 110 kPa) or the use of strong chemicals (such as sodium hydroxide and sulfuric acid). Treatments such as autoclaving, steam explosion and alkali treatment are preferably avoided.

The quality of the lignin obtainable by the methods of the invention may be attributed to a combination of waste processing as outlined below, followed by enzymatic hydrolysis according to the present invention.

The lignocellulose component from MSW may be obtained by:

(a) separating MSW into at least two parts, comprising: (i) mainly food waste (fines) and (ii) mainly paper and other recyclable material (overs);

(b) pulping the overs; and (c) washing the overs to obtain a cellulose-rich biomass; and optionally (d) processing the fines to obtain a cellulose-rich biomass.

Butanosolv extraction of PHS enables isolation of lignin with a high β-O-4 content that could be selectively functionalised to yield, for example, PEG-modified or fluorescent lignin. Furthermore, depolymerisation of this lignin would enable the isolation of pure monomers with low conversion or mixtures of monomers with high conversion, based on existing literature methods.

The lignin component of the PHS contains or comprises at least about 20%, 25%, 30%, 35%, 40%, 45%, 50% or more intact β-O-4 bonds per 100 C9 units. The at least about 20% intact β-O-4 bonds available for chemical transformation is comparable to other high β-O-4 content reference lignins such as walnut shell and douglas fir.

Additionally or alternatively, the PHS has a higher calorific value relative to PHS obtained from conventional hydrolysis methods and/or compared to lignocellulosic biomass obtained from non-MSW sources, and/or relative to the original lignocellulosic biomass starting material. The calorific value (CV) of the PHS obtainable or obtained by the method of the invention is 20-25 MJ $kg^{-1}$, whereas cellulose and the starting lignocellulosic biomass has a CV of 17 MJ $kg^{-1}$.

According to a second aspect of the present invention, there is provided sugar(s) obtainable or obtained by the method of the invention. The sugars may, for example, include glucose, xylose, mannose, galactose, arabinose and soluble oligosaccharides containing chains of monomeric sugars. Preferably, the sugar solution obtained by the method of the invention contains glucose:xylose at a ratio of 5-8:1 or 6-7:1.

According to a third aspect of the present invention, there is provided a lignin-rich solid (refered to herein as the washed residual lignocellulosic biomass or post hydrolysis solids (PHS), the terms being used interchangably herein) obtainable or obtained by the method of the present invention, which PHS has a higher calorific value relative to PHS obtained from conventional methods and/or relative to the original lignocellulosic biomass starting material. The calorific value (CV) of the PHS obtainable or obtained by the method of the invention is 20-25 MJ $kg^{-1}$, whereas cellulose has a CV of 17 MJ $kg^{-1}$.

Additionally or alternatively, the PHS comprises less than about 6% ash or less than about 7% ash or less than about 8% ash or less than about 9% ash or less than about 10% ash.

Additionally or alternatively, the PHS also comprises a lignin and/or pseudo lignin component. The lignin component of the PHS contains or comprises at least about 20%, 25%, 30%, 35%, 40%, 45%, 50% or more intact β-O-4 bonds per 100 C9 units.

PHS can be pelletised and sold as an engineered fuel for use in combustion, gasificaton and pyrolysis processes. The virigin lignin content in the PHS could also be treated with enzymes, bacteria or fungi to produce various value added products, such as specialty chemicals and aromatic/ring-containing bio-material building blocks. The lignin inside the PHS contains or comprises at least about 20% intact β-O-4 bonds per 100 C9 units. Furthermore, the PHS may also comprise less than about 6% ash or less than about 7% ash or less than about 8% ash or less than about 9% ash or less than about 10% ash The PHS also comprise lignins and/or pseudo lignins.

According to a fourth aspect of the present invention, there is provided use of such sugars for biogas production and/or PHS for gasification or pyrolysis, and for example to create value added products, such as specialty chemicals, e.g. bio-resins, lactic acid, butanol, succinic acid, syngas etc. These bio-resins have a lower greenhouse gas (GHG) footprint, and their physical properties such as parting strength and stiffness are within the tollerance limits of bio-resins made with food-crop or industrial sugar.

Also provided is the use of one or more surfactants and/or one or more nitrogen additives, such as PEG, for reducing the enzyme quantity needed during hydrolysis of a lignocellulosic biomass (particularly from MSW) and/or for increasing sugar yield from a lignocellulosic biomass (particularly from MSW).

According to a fifth aspect of the present invention, there is provided a method for making fuel, comprising converting a high solids concentration of lignocellulosic biomass, preferably obtained from MSW, by performing the method of the invention to obtain sugars and/or PHS and the use thereof in biogas production, gasification or pyrolysis.

According to a sixth aspect of the present invention, there is provided a hitherto unknown composition for use in enzyme hydrolysis of a lignocellulosic biomass, particularly from MSW, comprising cellulases and at least one surfactant and/or phosphoric acid and/or biocide agents such as chlorine dioxide, Benzoisothiazolinone, virginiamiacin and/or buffering agents such as calcium carbonate. Any surfactant and/or or nitrogen-containing additive may be used; one or more of Tween, glycine, preferably PEG, particularly PEG 6000, is preferred. The cellulase and/or hemicellulase may be xylanases and mannases, preferably, both cellulases and hemicellulases are comprised in the composition.

According to a seventh aspect of the present invention, there is provided a biorefinery for refining a high solids concentration of lignocellulosic biomass, preferably obtained from MSW, by performing the method of the invention to produce sugars, fuel, feed for biogas production, gasification or pyrolysis, and for example, to create value added products, such as specialty chemicals e.g. bio-resins, lactic acid, butanol, succinic acid etc.

Performing the methods of the invention advantageously results in a high glucan conversion (80+ %) and a high sugar (glucose) concentration (8+ wt %) after combining the hydrolysates of the first and second stage of hydrolysis. The high glucan conversion means that the amount of unconverted cellulose in the substrate is minimised. Nevertheless, any residual solid associated sugar could be used for biogas production. Gasification, pyrolysis, enzyme, bacterial or fungal modification could be employed using the PHS as a substrate to create various value added products. The integration of the production of sugar and chemicals would allow for MSW as a substrate to be successfully used as a feedstock for a sugar-and-lignin platform bio-refinery.

Preferred features of the second, third, fourth, fifth, sixth and seventh aspects of the invention may be as described above in connection with the first or any other aspect.

Throughout the description and claims of this specification, the words "comprise" and "contain" and variations of the words, for example "comprising" and "comprises", mean "including but not limited to", and do not exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Other features of the present invention will become apparent from the following examples. Generally speaking the invention extends to any novel one, or any novel combination, of the features disclosed in this specification (including any accompanying claims and drawings). Thus features, integers, characteristics, compounds, chemical moieties or groups described in conjunction with a particular aspect, embodiment or example of the invention are to be understood to be applicable to any other aspect, embodiment or example described herein unless incompatible therewith.

Moreover, unless stated otherwise, any feature disclosed herein may be replaced by an alternative feature serving the same or a similar purpose.

FIGURES

The present invention will now be described with reference to the following Figures which are by way of illustration alone, in which.

EXAMPLES

The present invention will now be described with reference to the following examples, which serve to illustrate the invention, and which are not intended to limit the scope of the invention.

A. Substrate

Substrate obtained from MSW was tested and found to show similar behaviour to other lignocellulosic materials even though the matrix may be considered more complex. The MSW substrate was further investigated to observe the effect on hydrolysis performance of: (i) particle size or fibre length; (ii) the presence of extractives such as oils, waxes and other solvent soluble compounds; (iii) the presence of lignin; (iv) the presence of calcium carbonate; and (v) the presence of pseudo lignin. Manipulation strategies trialled to address these factors were: (i) milling to 0.5 mm to reduce particle size and floc forming capacity and to decrease crystallinity; (ii) extractives removal with 1% sodium hydroxide or acetone to increase cellulose accessibility; (iii) lignin removal with sodium chlorite and acetic acid to improve substrate accessibility; (iv) calcium carbonate removal with sulphuric acid or neutral detergent washing to improve substrate accessibility; (v) pseudo-lignin removal with diluted sulphuric acid soaking to improve substrate accessibility.

(i) Milling

Method Summary: Dried pulp was milled to 0.5 mm in a centrifugal shearing mill, and the resulting pulp was hydro-lysed at 8% TS with 35 mg C-Tec2 g-1 pulp for 3 days in 7 mM citric acid buffer to maintain the pH of the hydrolysis system at 5. Unmilled dried MSW pulp was run under the same conditions to act as a control. The composition of the milled and unmilled substrate was 63:9:7:10:2 of glucan: xylan:mannan/araban/galactan:lignin:ash.

Results: The glucan conversion over a 3-day hydrolysis period of pulp milled to less than 0.5 mm was 57.5%, while unmilled pulp achieved a conversion of 64.4%. The milling treatment used did not improve the hydrolysability of the pulp and in fact decreased the hydrolysis yield.

(ii) Extractives Removal

A number of pre-treatments were carried out to alter the substrate by removing compounds such as extractives or lignin, which could potentially hinder hydrolysis. After removal of these compounds, the substrate was hydrolysed to see the effect of the various treatments.

Note: All experiments in this section were carried out with 50 mg enzyme $g^{-1}$ pulp so that the systems were not enzyme limited and it was possible to determine what effects the various treatments had on the hydrolysis potential.

Method summary: Extractive removal was trialled using acetone and 1% NaOH extraction. The MSW pulp was dried and milled to ≤0.5 mm to increase the accessible surface area. Extractives were first removed using a soxhlet extractor in combination with either a solvent (acetone) or a weak alkali (1% NaOH). After extraction, the substrates were washed thoroughly in deionised water to return the pH to neutral. Hydrolysis was carried out on two pulps and on an unextracted but milled control. The treated and untreated pulps were oven dried at 105° C. prior to hydrolysis and then diluted to 11% TS in water adjusted to pH 5 with phosphoric acid. The enzyme dose was based on total solids not glucan content and the enzyme loading was 50 mg C-Tec3 $g^{-1}$ (residual pulp i.e, after treatment).

Results & Discussion: Solvent extraction to remove extractives or pseudo lignin with acetone seemed to increase the substrate accessibility and led to an increase of up to 6% in conversion compared to unextracted pulp. This increase in conversion, however, would most probably not offset the cost of employing a solvent extraction step in a full-scale process unless the extraction procedure was also able to recover value-added compounds or building blocks. Mild alkali treatment led to a significant decrease in conversion, possibly due to deposition of compounds on the surface of the cellulose making it inaccessible.

(iii) Lignin Removal

Method summary: Lignin removal was performed using acetic acid and sodium chlorite on pulp 'as is' and on acetone-extracted pulp. In both cases the pulp was milled to ≤0.5 mm prior to the various treatments in order to increase the surface area. Following extraction and lignin removal the pulps were washed thoroughly in deionised water and oven dried at 105° C. overnight. The treated pulp and the control were hydrolysed with 50 mg C-Tec3 $g^{-1}$ residual pulp. SEM images were taken of the lignin-extracted pulp only (i.e. not of the acetone & lignin extracted pulp).

Results & Discussion: Lignin extraction using sodium chlorite and acetic acid only showed limited success and SEM imaging of the material indicated that it led to surface deposits or structural changes which reduced cellulose accessibility. The complex nature of the substrate and the many processing steps it has been through prior to hydrolysis may mean the lignin is not susceptible to removal, this is particularly the case with paper and cardboard. From these various extraction treatments it was concluded that any extractives or lignin present in the substrate do not significantly hinder substrate conversion.

(iv) Calcium Carbonate Removal

Methods summary: Two methods were tested for removal of calcium carbonate from samples of pulp milled to ≤0.5 mm: a) a sulphuric acid wash and b) a neutral detergent (ND) wash. The sulphuric acid pulp washing procedure was taken from Wang et al., (2011b). Acid washing involved mixing 50 g of MSW pulp with 20 mL acid solution ($H_2SO_4$) at the hydrogen ion concentration 0.1 mol L-1. 500 mL of deionized water was then added and the mixture was stirred for 10 minutes. The acid solution was removed by squeezing by hand. The procedure was repeated three times, and then the pulp was washed in deionized water until the pH was 5.0. The pulp was then oven dried overnight at 105° C. The second treatment used neutral detergent as in the Fibercap fibre analysis (Kitcherside et al., 2000). The pulp was boiled in neutral detergent and subsequently washed thoroughly until pH 7 was reached, then dried. Once dried, both pulps underwent compositional analysis and hydrolysis at 10% TS with 50 mg C-Tec3 $g^{-1}$ residual pulp in water adjusted to pH 5 with phosphoric acid. An untreated and unmilled pulp was used as the control.

Results: The hydrolysis results show that the MSW pulp, sulphuric acid washed pulp and neutral detergent washed pulp had glucan conversions of 54±1%, 53±2%, and 36±1% respectively. In terms of glucose yield in hydrolysate this corresponded to 3.6±0.1, 3.3±0.1, and 2.6±0.1 wt %. Although the conversions of the MSW pulp and the sulphuric acid washed pulp were the same, the compositional analysis of the control pulp showed a slightly higher glucose content. Thus the absolute glucose yield from control pulp was higher than from the $H_2SO_4$ washed pulp.

B. Enzyme Enhancement

The following experiments were carried out to determine whether employing various additives or changing the reaction medium could have a positive effect on hydrolysis: (i) Nitrogen addition in the form of glycine to help reduce any unproductive binding of enzymes; (ii) pH control with buffer vs no buffer to determine whether the buffer caused a decrease in substrate accessibility, enzyme performance or water availability; (iii) surfactant/polymer additive in the form of PEG 6000 to help reduce any unproductive binding of enzymes and to increase enzyme activity; (iv) addition of ascorbic acid to determine whether the substrate had a sufficient redox factor to help catalyse hydrolysis and (v) diluted sluphuric acid soaking pre-treamtent.

(i) Nitrogen Additive

Method Summary: Low solids enzyme hydrolysis was performed with the addition of glycine to pH 5 citric acid buffer with phosphoric acid, at 1, 2 and 5 wt % prior to substrate dilution and hydrolysis. The pH of the solutions was also checked and if required re-adjusted to pH 5 after glycine addition. The hydrolysis was run at 12% TS and the reaction mixture was autoclaved for 15 minutes at 121° C. prior to enzyme addition of 50 mg enzyme $g^{-1}$ pulp. The hydrolysis was carried out over a 48-hour period.

Figure 2:
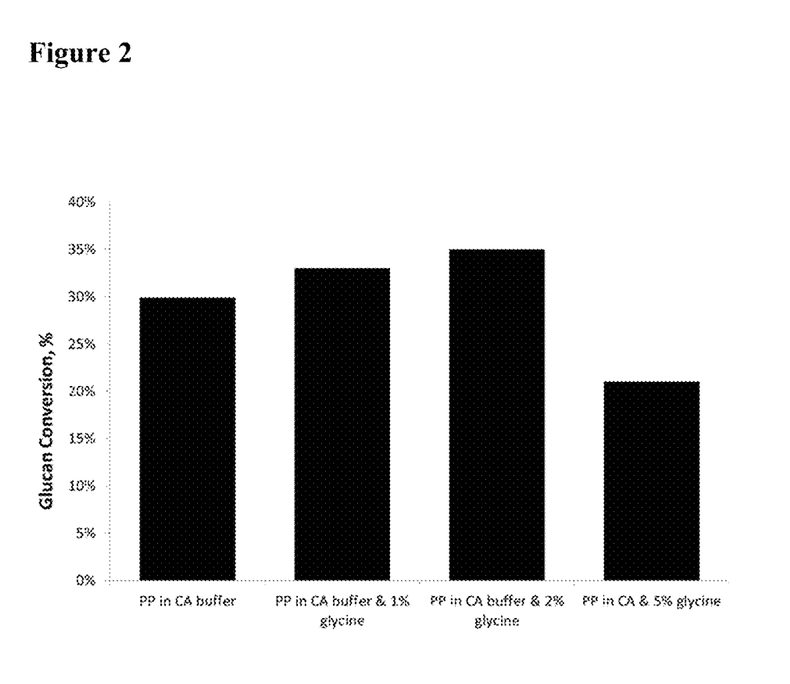
FIG. 2 shows glucan conversion of dried MSW pulp (PP) with the addition of glycine in citric acid buffer (CA). The hydrolysis was carried out using 11.5% TS and 50 mg C-Tec2 g-1 pulp over 3 days.

Results: The addition of glycine at 1-2 wt % in the reaction medium increased the percentage glucan conversion by 3-5%, whereas addition of 5% glycine concentration caused a dramatic 9% decrease in glucan conversion. The results are shown in FIG. 2.

(ii) pH Control With Buffer Vs No Buffer

Phosphoric acid is commonly used in industry to adjust the pH of a reaction medium. The use of an acid is also preferable to a buffer for processing large quantities of material, as buffers can be expensive and require a range of chemicals. In this instance it is not crucial to maintain the pH at 5, and as such a buffer is not strictly required. For these reasons it was of interest to see if there was any difference in hydrolysis yield when using phosphoric acid for pH adjustment as compared to citric acid buffer.

Method Summary: Hydrolysis was carried out in either 7 mM citric acid buffer at pH 5 or water adjusted to pH 5 with phosphoric acid. Dried MSW pulp was diluted to 12.5% TS and autoclaved at 121° C. for 15 minutes after which the temperature of the wet pulp was brought down to 50° C. The pulp was charged with 50 mg C-Tec2 g-1 pulp and left to hydrolyse for 3 days.

Figure 3:
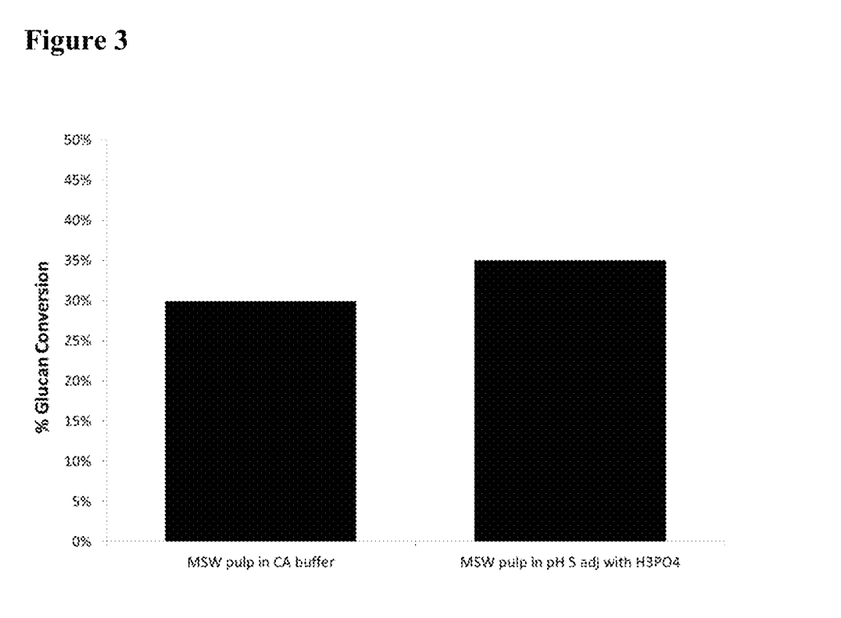
FIG. 3 shows glucan conversion of MSW pulp in either 7 mM citric acid buffer at pH 5 or water adjusted to pH 5 with phosphoric acid. Hydrolysis was carried out for 3 days with 12.5% solids using 50 mg C-Tec2 g-1 pulp.

Results: A 5% increase in glucan conversion (overall conversion 35%) was seen for the MSW pulp hydrolysed using phosphoric acid for pH control compared to using citric acid buffer (30% glucan conversion). The results are shown in FIG. 3.

(iii) Surfactant/Polymer Additive

As glycine showed a positive effect on a low solids hydrolysis it was of interest to determine whether a more widely used additive, PEG 6000, would also give an increase in yield, especially at high solids.

Method Summary: Hydrolysis was carried out 20% TS with 30 mg C-Tec3 $g^{-1}$ pulp in pH 5 water containing 0.6 wt % PEG 6000. Wet MSW pulp was diluted from 40% TS with pH 5 dilution water containing 1% PEG to give a final concentration of 0.6% PEG in the reaction medium. The enzyme was added directly after dilution and hydrolysis was carried out for 6 days.

Figure 4:
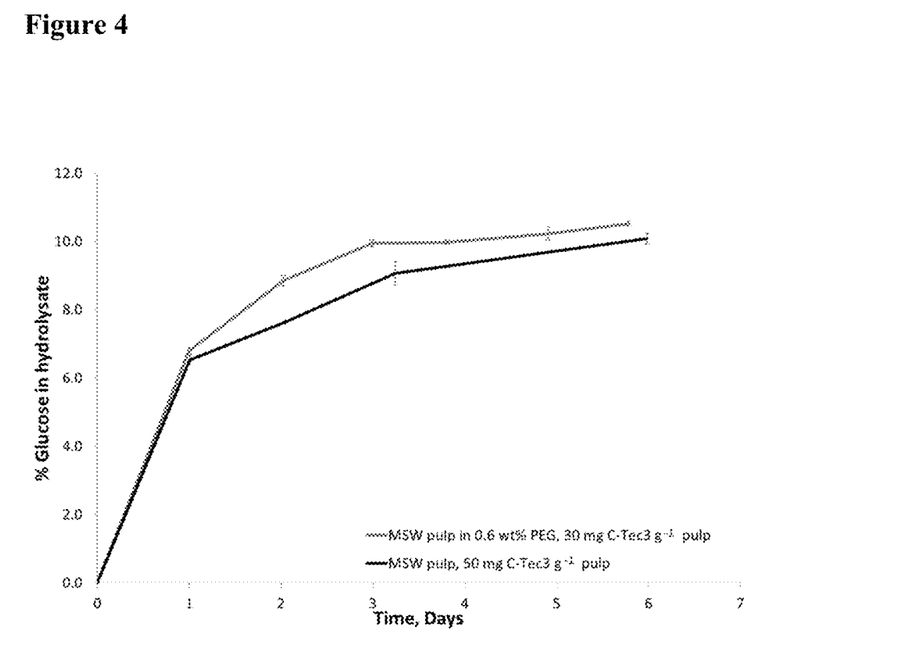
FIG. 4 shows hydrolysate glucose concentrations over time from hydrolysis of 20% TS pulp with 30 mg C-Tec3 g-1 pulp and 0.6% PEG (grey) and with 50 mg C-Tec3 g-1 pulp without PEG (black). Error bars represent range.
Figure 5:
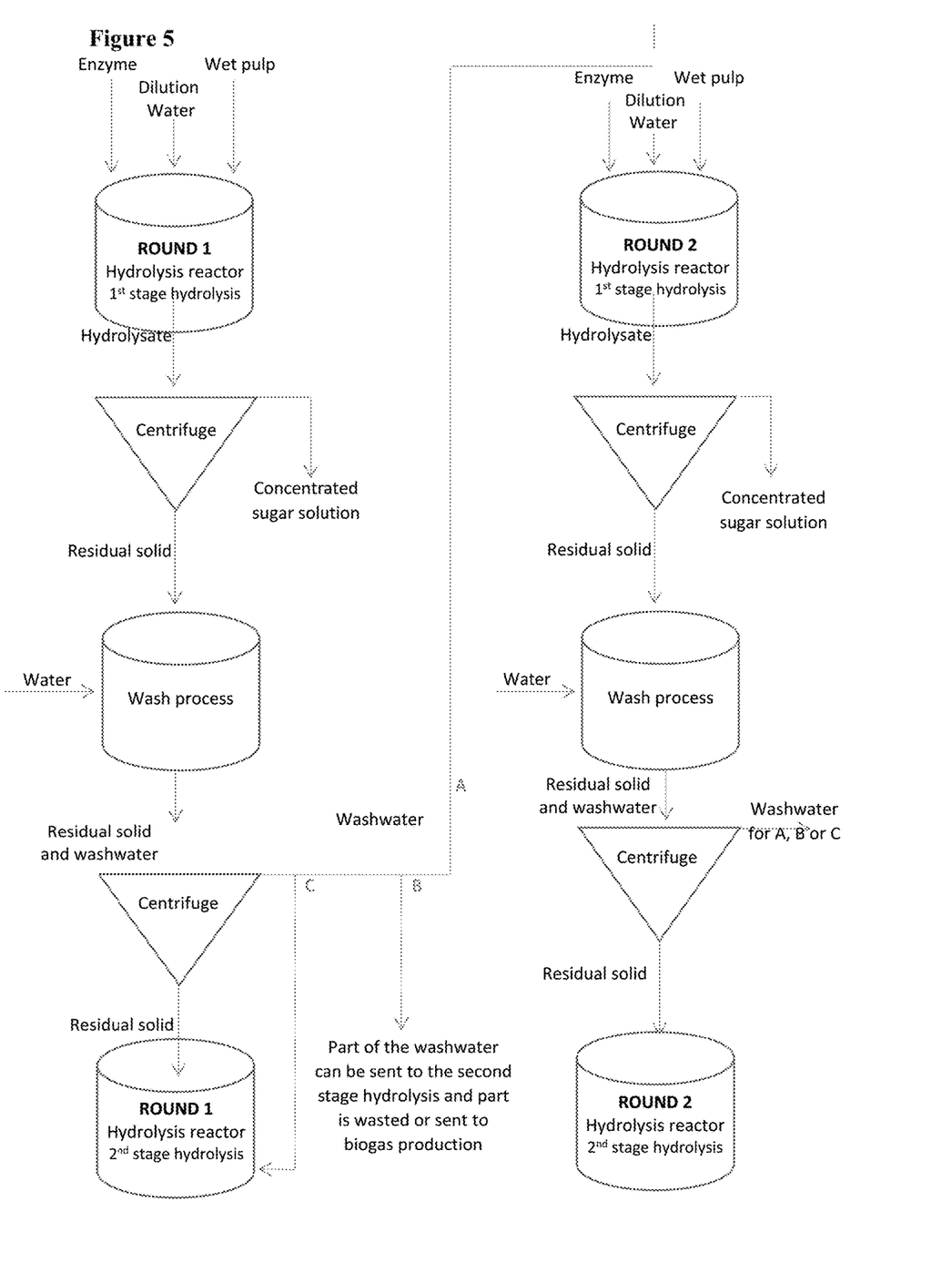
FIG. 5 shows a schematic diagram of the general process sequence for the wash water recycle procedure.
Figure 6:
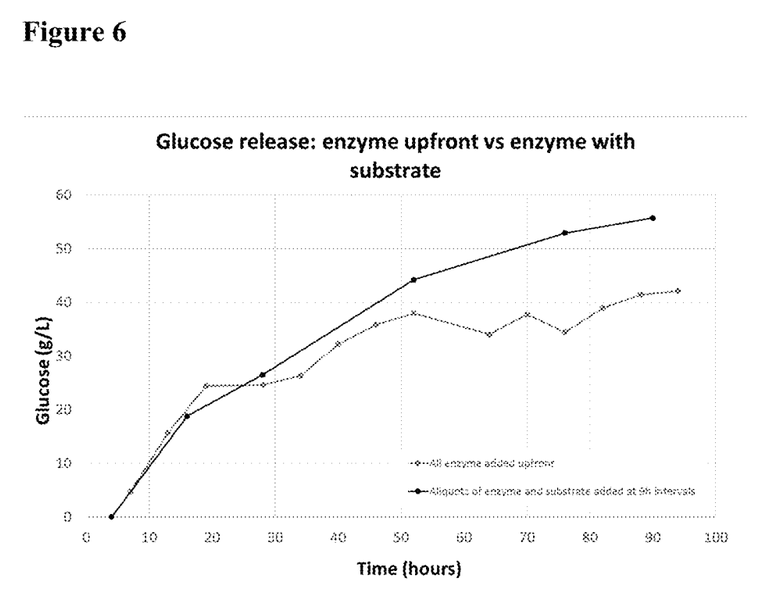
FIG. 6 shows glucose yield (g/L) during hydrolysis when comparing fed batch hydrolysis with all enzyme upfront and semi-continuous lignocellulosic biomass addition (grey) and semi-continuous addition of enzyme and lignocellulosic biomass (black).

Results: The results are shown in FIG. 4. As can be seen, the glucose concentrations for MSW pulp hydrolysed with 30 mg C-Tec3 $g^{-1}$ pulp in the presence of 0.6% PEG, and MSW pulp hydrolysed with 50 mg C-Tec3 $g^{-1}$ pulp without PEG addition. From these results it is clear that the use of PEG results in a greater substrate conversion with less enzyme than hydrolysis of pulp without PEG. Over 6 days the hydrolysate containing PEG and a lower enzyme dosage achieved a conversion of 76±1%, whereas the control with the higher enzyme dose and no PEG achieved a conversion of 74±1%, equivalent to glucose yields in the hydrolysate of 10.1±0.1 and 10.5±0.2 wt % respectively. This shows that the use of PEG allows a 40% decrease in the enzyme requirement.

A further experiment was conducted in which the same amount of enzyme (30 mg $g^{-1}$ pulp) was used with and without the addition of PEG. Results showed that the addition of PEG resulted in a 15±1% increase in conversion over 48 hours. The glucose yields and glucan conversions from the experiment without PEG and that with the additive were 6.4±0.0 wt % (44±1%) and 8.3±0.3 wt % (59±2%) respectively. This results is not presented graphically.

Discussion: The result shown here is contradictory to that from other MSW studies where PEG has been used. Here it is clear that PEG enhances conversion but in other studies this has not been the case (Jensen et al., 2011; Kemppainen et al., 2014).

(iv) Addition of Ascorbic Acid

Objective: To determine whether the MSW pulp contained sufficient redox activity to allow maximal enzyme activity by the LPMO compound AA9.

Method Summary: To establish an appropriate concentration range an initial test was carried out in which Fisher brand filter paper was hydrolysed at a solids content of 4.5% TS. The water used for dilution contained varying concentrations of ascorbic acid (0.07, 0.13, 0.20 and 0.41 wt %). The MSW pulp was then tested at a solids concentration of 10.5% TS, where the pulp was diluted with pH 5 water containing 0.13 wt % ascorbic acid. An enzyme concentration of 50 mg C-Tec3 g-1 pulp was used for both the filter paper and the MSW pulp and hydrolysis was conducted for 3 days.

Results: Addition of ascorbic acid at 0.13% in the liquid medium was the optimum concentration for increased filter paper conversion. This resulted in a 13% increase in glucan conversion above that achieved for filter paper with no ascorbic acid. The presence of ascorbic acid was however found to have little or no effect on achievable hydrolysis of MSW pulp. Thus, following 3-days of hydrolysis 53% conversion was obtained both with and without the additive. This indicates the the MSW derived lignocellulose contains sufficient redox activity to allow for efficient operation of the LPMO enzyme complex.

v) Diluted Sluphuric Acid Soaking Pre-Treatment

Objective: to determine the effect of removing pseudo-lignin with a dilute sluphuric acid soaking pre-treamtent Method Summary: Newspaper and recycled paper are a large fraction of lignocellulosic biomass derived from MSW. These materials are highly recalcitrant and not easily degradable by enzyme hydrolysis. Newspaper was shredded using an office shredder, and soaked with 1% vol sulpuric acid in a ratio liquid/solid equal to 3.3 for 3 hours at room temperature. The resulting material was washed thouroughly with tap water and hydrolysed with 30 mg enzyme $g^{-1}$ pulp.

Results: Between 85.5 and 100% of the pseudo-lignin was removed during the pre-treatment. Additionally, close to 100% of the calcium carbonate was removed resulting in a material enriched in carbohydrate. A 21% increase in glucan conversion was achieved when using this pre-treated material.

C. Substrate and Enzyme Feeding Strategies

Different substrate and enzyme feeding strategies can affect the conversion efficiency of lignocellulosic substrates. A number of feeding strategies were tested to observe their effect on final hydrolysis yield and to determine the best conditions for high solids hydrolysis. The strategies trialled were all enzyme up front with semi-continuous aliquoted solids addition and coupled aliquots of enzyme and solids. The semi-continuous feeding strategy was trialled over a number of time intervals. In these experiments it was found that in a continuous stirred tank reactor it was not possible to perform batch hydrolysis with an ititial solids loading greater than 8% Total Solids. Semi-continuous aliquoted enzyme and solids hydrolysis up to 17% TS gave at least a 15% increase in sugar yield and up to 25% increase in sugar yield as compared to enzyme upfront and aliquoted solids additions if surfactant was added to the reaction medium and the reaction was left to run for an increased period of time. These results were obtained when using a 9 hour interval between additions. When the interval time was reduced to 3 h the yield increased by a further 5% and the agitation load on the reactor was reduced.

D. Optimisation of High Solids Hydrolysis Process

The aim of this work was to investigate and optimise the hydrolysis of MSW derived pulp under industrially relevant conditions. It was therefore necessary to consider parameters that would be of importance in a large-scale commercial context, such as relatively short process times, high conversion rates and yields and minimal enzyme dosing. The overall goal was to maximise the efficiency of enzyme usage to obtain a concentrated sugar solution from a waste feedstock, without compromising yields or prolonging process times.

(i) Two-Stage Hydrolysis With Intermediate Product Removal

Objective: To determine the effect on hydrolysis yield by removing a portion of the liquid in the hydrolysate, which contains product sugars, and replacing this with water.

Method Summary: Hydrolysis was carried out at 25% TS with 50 mg C-Tec2 or C-Tec3 $g^{-1}$ pulp for 48 hours. The resulting hydrolysate was centrifuged and the concentrated sugar solution was removed and replaced with water adjusted to pH 5 with phosphoric acid without any additional enzyme. The hydrolysis was then allowed to continue for a further 2-4 days either with or without another product removal step.

Results: For the glucan conversion in the experiment carried out with C-Tec2, glucan conversion in the first 48 hours was approximately 29%. The sugar solution was then removed from the mixture and replaced with pH 5 water. The following 2 days of hydrolysis produced an overall 4-day conversion of 48%, which is 9% higher than the control experiment with no sugar removal.

The experiment was repeated with C-Tec3 and the concentrated sugar solution was removed at day 2 and day 4. In this experiment both the control and the product removal experiment (PRE) had an average 2-day conversion of 36%. After 4 days of hydrolysis, the conversion of the control and the PRE were ~43% and ~47% respectively. By the end of the experiment, at 7 days, both the control and the PRE had achieved a similar conversion (49±3% and 51±3% respectively).

(ii) Two-Stage Hydrolysis With Intermediate Product Removal and Wash Step

When working at high solids concentrations there is significant retention of liquid within the residual solids. After a 48-hour hydrolysis at 20% TS, the residual solids from a centrifuged hydrolysate typically contain 35% solids, inclusive of sugar. This means that on average 43-45% of the hydrolysate liquid is extractable whilst 55-57% remained with the MSW pulp. The liquid remaining with the solid therefore represents a considerable amount of unrecovered sugar. The next sets of experiments were thus designed to recover as much of this residual sugar as possible for use in production of ethanol or other value-added products whilst also preventing product inhibition and improving water availability.

Objective: To determine whether enzyme activity could be increased by reducing the concentration of product sugars associated with the residual solid in the hydrolysate to less than 2 wt % glucose.

Method Summary: Part (A) Hydrolysis was carried out for 48 hours at 18.5% TS using 55 mg C-Tec3 $g^{-1}$ pulp, after which the hydrolysate was centrifuged and the concentrated sugar solution removed. The residual solid was washed with pH 5 water for one hour. The washwater was then removed by centrifugation and fresh pH 5 water was added to make up the volume of hydrolysate to the original volume before removal of the concentrated sugar solution. No extra enzyme was added in this process.

Results: The results show that when a pulp of 18.5% TS was hydrolysed for 48 hours with 55 mg CTec3 $g^{-1}$ pulp and washed at pH 5, the sugar concentration in the residual solids reduced from ~9.5 wt % to ~1 wt %. The second stage hydrolysis of the re-suspended solids resulted in a further 14% of glucan conversion, taking the total conversion efficiency from 67.2±1.3% to 81.2±0.7%. This result can be compared with that for a control which did not undergo product removal and a wash step, and had an overall conversion efficiency of 68.0±5.0%. The results suggest that the increase in total conversion efficiency is due to an improvement in water availability brought about by removal of the residual sugars. Analysis of the hydrolysate from the secondary hydrolysis showed a slight increase (1.1 fold) in cellobiose concentration as compared to the initial hydrolysis, indicating a possible loss of β-glucosidase from the original hydrolysate.

(iii) Washwater Reuse in Subsequent Hydrolysis

A further strategy was trialled in which the washwater from an intermediate wash step was used as the dilution water in a subsequent batch hydrolysis. This showed no detrimental effects on glucan conversion, while the glucose concentration in the hydrolysate was increased due to augmentation by the 1 wt % glucose in the washwater. Enzyme recovery in the washwater was increased if the residual solid was washed at pH 9 rather than 5.

From these results it was clear that a split hydrolysis (i.e. one with a first and second stage and an intermediate wash step) was promising in achieving high glucose yields and obtaining a high overall glucan conversion. A continuous hydrolysis process was therefore tested where washwater from one hydrolysis was used as the dilution water in a subsequent hydrolysis over 3-6 rounds. This was undertaken in order to maximise the yield of sugars and to determine whether any carryover of enzyme activity could be seen. This washwater recycle strategy was carried out with wash conditions at pH 3-5, 7, 9+ and pH 5 and 7 with the addition of PEG 6000. Of these the two most promising strategies were those using an alkaline wash and that using a PEG 6000 wash at a concentration of 0.25 w % in the reaction medium. In addition to the continuous first stage hydrolysis process a second-stage hydrolysis was performed within some of the strategies without the addition of extra water at pH 5 and this gave an increase in glucan conversion of up to 28%. An alkaline wash gave an increase in glucan conversion of 5% between round 1 and round 3 or 4, possibly indicating enzyme carryover. In this strategy a glucose concentration of up to 8.2% was achieved in the first stage of hydrolysis. When using PEG it was unclear whether enzyme carryover occurred between the rounds, and further investigation is needed to clarify this. Furthermore this additive caused a pH buffering effect which resulted in the pH of hydrolysate settling below the optimal level. Despite this, it was possible to obtain consistent glucose concentrations above 7.3 wt % in the hydrolysates of the first-stage and this could probably be improved upon with further process optimisation. The most important result came from the third round of this strategy when using a pH 7 wash and 0.25 wt % PEG, with solids contents of 20% TS and 17% TS (after 48 hours of hydrolysis) in the first and second stages of hydrolysis. This gave a total glucan conversion of 81% with a 40% reduction in the required enzyme dosing. Mixing of the hydrolysates from the first and second stages would have given a final concentration of 8+ wt % glucose. This finding demonstrates that it is possible to obtain a high sugar yield coupled with high substrate conversion when using a high initial solids content which has not previously been demonstrated. The total obtainable sugar yield of monomeric and oligomeric sugars would be 10+ wt %.

The results therefore show an effective hydrolysis method for MSW pulp at a relatively low enzyme loading (30 mg C-Tec3 $g^{-1}$ pulp) under high solids conditions (20% TS). A high glucan conversion (80+ %) was achieved with a high sugar content (8+ wt %) reducing the need for further concentration of the hydrolysate. Obtaining a high glucan conversion minimises the amount of unconverted cellulose in the substrate. This residual solid and associated sugar could be used for biogas production, and gasification or pyrolysis could be employed to the resiudal solid to create various value added products. By integrating the production of sugar and chemicals, this substrate can be used successfully as a feedstock for a sugar-lignin platform bio-refinery.

REFERENCES

Jensen, J. W., Felby, C., Jorgensen, H. 2011. Cellulase Hydrolysis of Unsorted MSW. *Applied Biochemistry and Biotechnology*, 165(7-8), 1799-1811.

Kemppainen, K., Siika-aho, M., Östman, A., Sipilä, E., Puranen, T., von Weymarn, N., Kruus, K. 2014. Hydrolysis and composition of recovered fibres fractionated from solid recovered fuel. *Bioresource Technology*(0).

Kitcherside, M. A., Glen, E. F., Webster, A. J. F. 2000. FibreCap: an improved method for the rapid analysis of fibre in feeding stuffs. *Animal Feed Science and Technology*, 86(1-2), 125-132.

Sluiter, A., Hames, B., Ruiz, R., Scarlata, C., Sluiter, J., Templeton, D., Crocker, D. 2011. Determination of Structural Carbohydrates and Lignin in Biomass, http://www.nrel.gov/biomass/analytical_procedures.html#lap-009. NREL, Golden, Colo., USA.

Wang, X., Song, A., Li, L., Li, X., Zhang, R., Bao, J. 2011b. Effect of calcium carbonate in waste office paper on enzymatic hydrolysis efficiency and enhancement procedures. *Korean Journal of Chemical Engineering*, 28(2), 550-556.

Xue, Y., Jameel, H., Park, S. 2012a. Strategies to Recycle Enzymes and Their Impact on Enzymatic Hydrolysis for Bioethanol Production. *Bioresources*, 7(1), 602-615.

The invention claimed is:

1. A method for increasing sugar yield from a high solids concentration of lignocellulosic biomass and/or for reducing enzyme quantity, the method comprising:

a. enzymatic hydrolysis of a lignocellulosic biomass to obtain a slurry, wherein the hydrolysis comprises more than two aliquot additions of enzyme and lignocellulosic biomass;
b. removal of sugars from the slurry to obtain a residual lignocellulosic biomass and washing of the residual lignocellulosic biomass to obtain washed residual lignocellulosic biomass; and
c. hydrolysis, without enzyme addition, of the washed lignocellulosic biomass obtained from step b;
wherein said sugars comprise glucose: xylose at a ratio of 5-8: 1 and/or wherein said washed residual lignocellulosic biomass comprises (i) less than about 6% ash and/or (ii) a lignin component comprising at least about 20% intact β-O-4 bonds per 100 C9 units,
wherein the method does not include any pre-treatment by milling or treatments which require a temperature above 130° C., a pressure above 110 kPa or the use of a strong acid or strong base.

2. The method according to claim 1 comprising further repeating steps b. and c.

3. The method according to claim 1, wherein said lignocellulosic biomass is subjected to a pre-treatment to enhance cellulose breakdown and/or result in removal of some lignin and/or pseudo lignin prior to step a.

4. The method according to claim 3, wherein said pre-treatment comprises solvent extraction and/or cooking at about pH 5.

5. The method according to claim 1, wherein said enzyme of a. comprises cellulases and hemicellulases.

6. The method according to claim 1, wherein the enzymatic hydrolysis of a. is in the presence of at least one surfactant and/or at least one nitrogen additive.

7. The method according to claim 6, wherein said surfactant is glycine or PEG.

8. The method according to claim 7, wherein PEG is added in an amount ranging from between about 0.01-2% per g dry lignocellulosic biomass.

9. The method according to claim 7, wherein said surfactant is PEG6000.

10. The method according to claim 6, wherein said surfactant and/or nitrogen additive allows for a decrease in enzyme requirement and/or an increase in sugar yield and/or improved dewaterability.

11. The method according to claim 10, wherein said decrease in enzyme requirement allows for the same or greater sugar yields with about 10% less, 20% less, 30% less, 40% less, or 50% less enzyme.

12. The method according to claim 10, wherein said sugar yields are increased by at least 1%, 2%, 3%, 4%, 5%, 6%, 7%, 8%, 9%, 10%, 11%, 12%, 13%, 14%, 15%, 16%, 17%, 18%, 19%, or 20% compared to control reactions in the absence of a surfactant.

13. The method according to claim 1, wherein enzymatic hydrolysis of a. is conducted with agitation.

14. The method according to claim 1, wherein said washing of the residual lignocellulosic biomass comprises replacing existing water with water having a pH between about pH 5 and pH 9.

15. The method according to claim 1, comprising, at least four, at least five, at least six, at least seven, at least eight, at least nine or at least ten or more aliquot additions of enzyme and lignocellulosic biomass during one hydrolysis reaction.

16. The method according to claim 1, wherein said sugars are removed in b. from the slurry directly or by fermentation.

17. The method according to claim 1, wherein said lignocellulosic biomass is obtained from municipal solid waste (MSW) through a process, comprising:
(a) separating MSW into at least two parts, comprising: (i) fines comprising mainly food waste and (ii) overs comprising mainly paper and other recyclable material;
(b) pulping said overs; and
(c) washing said pulped overs to obtain a first cellulose-rich biomass; and optionally
(d) processing said fines to obtain a second cellulose-rich biomass.

18. A method for making fuel, comprising converting a high solids concentration of lignocellulosic biomass, according to the method of claim 1 and obtaining sugars and/or post hydrolysis solids (PHS) therefrom and converting said sugars into biogas and/or converting said PHS into syngas and/or gasification, combustion or pyrolysis of said PHS.

19. The method according to claim 18, wherein the lignocellulosic biomass is obtained from municipal solid waste.

20. A method for making specialty chemicals comprising converting a high solids concentration of lignocellulosic biomass, according to the method of claim 1 and obtaining sugars and/or post hydrolysis solids (PHS) therefrom and converting said PHS into specialty chemicals selected from the group consisting of bio-resins, lactic acid, butanol, succinic acid, and biomaterials.

21. The method according to claim 20, wherein the lignocellulosic biomass is obtained from municipal solid waste.

22. The method according to claim 1, wherein the lignocellulosic biomass is obtained from municipal solid waste.

* * * * *